(12) United States Patent
Akporiaye et al.

(10) Patent No.: US 7,070,999 B1
(45) Date of Patent: Jul. 4, 2006

(54) APPARATUS AND METHOD FOR GENERATING A PLURALITY OF ISOLATED EFFLUENTS

(75) Inventors: Duncan E. Akporiaye, Oslo (NO); Maureen L. Bricker, Buffalo Grove, IL (US); Ivar M. Dahl, Oslo (NO); Arne Karlsson, Oslo (NO); Charles P. McGonegal, Addison, IL (US); Elisabeth M. Myhrvold, Jar (NO); Martin Plassen, Oslo (NO); Svend A. Taftø, Sandvika (NO)

(73) Assignee: UOP LLC, Des Plaines, IL (US)

( * ) Notice: Subject to any disclaimer, the term of this patent is extended or adjusted under 35 U.S.C. 154(b) by 591 days.

(21) Appl. No.: 10/288,602

(22) Filed: Nov. 4, 2002

Related U.S. Application Data

(63) Continuation-in-part of application No. 09/954,461, filed on Sep. 17, 2001, now Pat. No. 6,808,685.

(51) Int. Cl.
*G01N 31/10* (2006.01)

(52) U.S. Cl. ...................................................... 436/37

(58) Field of Classification Search ................ 436/37
See application file for complete search history.

(56) References Cited

U.S. PATENT DOCUMENTS

| | | | |
|---|---|---|---|
| 5,304,354 A | 4/1994 | Finley et al. | 422/196 |
| 5,489,726 A | 2/1996 | Huss, Jr. et al. | 585/671 |
| 5,609,826 A | 3/1997 | Cargill et al. | 422/99 |
| 5,612,002 A | 3/1997 | Cody et al. | 422/131 |
| 5,746,982 A | 5/1998 | Saneii et al. | 422/134 |
| 5,766,556 A | 6/1998 | DeWitt et al. | 422/131 |
| 5,785,927 A | 7/1998 | Scott et al. | 422/104 |
| 5,792,431 A | 8/1998 | Moore et al. | 422/134 |
| 6,149,882 A * | 11/2000 | Guan et al. | 422/211 |
| 6,342,185 B1 | 1/2002 | Dahl et al. | 422/82.12 |
| 6,368,865 B1 | 4/2002 | Dahl et al. | 436/37 |
| 2003/0040116 A1 | 2/2003 | Canos et al. | 436/37 |

FOREIGN PATENT DOCUMENTS

| | | |
|---|---|---|
| DE | 198 09 477 A1 | 9/1999 |
| WO | WO 96/11878 A1 | 4/1996 |
| WO | WO 97/30784 A1 | 8/1997 |
| WO | WO 97/32208 A1 | 9/1997 |
| WO | WO 98/07026 A1 | 2/1998 |
| WO | WO 98/36826 A1 | 8/1998 |
| WO | WO 99/19724 A1 | 4/1999 |
| WO | WO 99/34206 A1 | 7/1999 |

(Continued)

OTHER PUBLICATIONS

Akporiaye, D. E.; Dahl, I. M.; Karlsson, A.; Wendelbo, R. Angew Chem. Int. Ed. 1998, 37, 609-611.

(Continued)

*Primary Examiner*—Yelena G. Gakh
(74) *Attorney, Agent, or Firm*—John G. Tolomei; Frank S. Molinaro; Maryann Maas

(57) ABSTRACT

An apparatus and a method for rapidly generating and processing a plurality of isolated effluents have been developed. A specific embodiment involves screening a plurality of solids through simultaneously contacting the members of the plurality with a fluid, sequentially sampling the resulting fluids, and processing the resulting fluids to, for example, determine changes as compared to the feed fluid or as compared to other resulting fluids.

21 Claims, 4 Drawing Sheets

FOREIGN PATENT DOCUMENTS

WO     WO 01 44801     6/2001
WO     WO 01 59463     8/2001

OTHER PUBLICATIONS

Bein, T. Angew. Chem. Int. Ed., 1999, 38, 323-326.

Cong, P.; Doolen, R. D.; Fan, Q.; Giaquinta, D. M.; Guan, S.; McFarland, E. W.; Poojary, D. M.; Self, K.; Turner, H. W.; Weinberg, W. H. Angew Chem. Int. Ed. 1999, 38, 484-488.

Holzwarth, A.; Schmidt, H.; Maier, W. F. Angew. Chem. Int. Ed., 1998, 37, 2644-2647.

Klien, J.; Lehmann, C. W.; Schmidt, H.; Maier, W. F. Angew Chem. Int. Ed. 1998, 37, 3369-3372;; and.

Senkam, S. M. Nature, Jul. 1998, 384(23), 350-353.

Taylor, S. J.; Morken, J. P. Science, Apr. 1998, 280(10), 267-270.

* cited by examiner

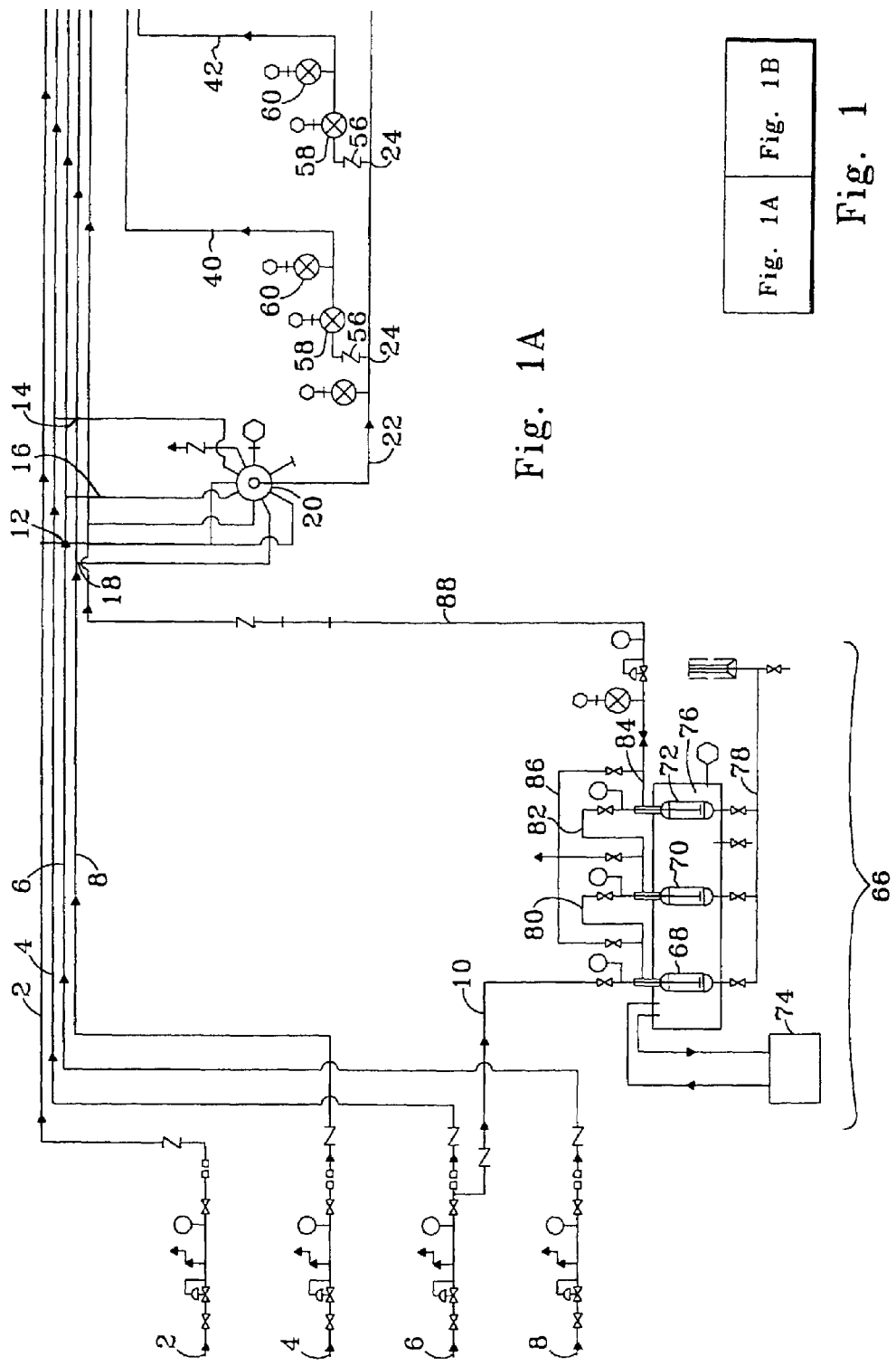

APPARATUS AND METHOD FOR GENERATING A PLURALITY OF ISOLATED EFFLUENTS

CROSS REFERENCE TO RELATED APPLICATION

This application is a continuation-in-part of our application U.S. application Ser. No. 09/954,461 filed Sep. 17, 2001 now U.S. Pat. No. 6,808,685, which is hereby incorporated by reference in its entirety.

FIELD OF THE INVENTION

The present invention relates to an apparatus and a method for rapidly generating a plurality of isolated effluents. A specific embodiment involves screening a plurality of solids through simultaneously contacting the members of the plurality with a fluid, sequentially sampling the resulting fluids, and processing the resulting fluids to, for example, determine changes as compared to the feed fluid or as compared to other resulting fluids.

BACKGROUND OF THE INVENTION

Developments in combinatorial chemistry have concentrated on the synthesis of chemical compounds. For example, U.S. Pat. No. 5,612,002 B1 and U.S. Pat. No. 5,766,556 B1 disclose a method and apparatus for multiple simultaneous synthesis of compounds. WO 97/30784-A1 discloses a microreactor for the synthesis of chemical compounds. Akporiaye, D. E.; Dahl, I. M.; Karlsson, A.; Wendelbo, R. Angew Chem. Int. Ed. 1998, 37, 609–611 disclose a combinatorial approach to the hydrothermal synthesis of zeolites, see also WO 98/36826. Other examples include U.S. Pat. No. 5,609,826, U.S. Pat. No. 5,792,431, U.S. Pat. No. 5,746,982, and U.S. Pat. No. 5,785,927, and WO 96/11878-A1.

More recently, combinatorial chemistry approaches have been applied to catalyst testing in an attempt to expedite the testing process. With the growing number of materials being synthesized combinatorially, more efficient methods of evaluating the materials are needed. Especially needed are combinatorial methods for the evaluation of solids that are designed to keep pace with the speed of combinatorial synthesis. For example, WO 97/32208-A1 teaches placing different catalysts in a multicell holder. The reaction occurring in each cell of the holder is measured to determine the activity of the catalysts by observing the heat liberated or absorbed by the respective formulation during the course of the reaction, and/or analyzing the products or reactants. Thermal imaging had been used as part of other combinatorial chemistry approaches to catalyst testing; see Holzwarth, A.; Schmidt, H.; Maier, W. F. Angew. Chem. Int. Ed., 1998, 37, 2644–2647, and Bein, T. Angew. Chem. Int. Ed., 1999, 38, 323–326. Thermal imaging may be a tool to gain knowledge of some semi-quantitative information regarding the activity of the catalyst, but it provides no indication as to the selectivity of the catalyst.

Some attempts to acquire information as to the reaction products in rapid-throughput catalyst testing are described in Senkam, S. M. Nature, July 1998, 384(23), 350–353, where laser-induced resonance-enhanced multiphoton ionization is used to analyze a gas flow from each of the fixed catalyst sites. Similarly, Cong, P.; Doolen, R. D.; Fan, Q.; Giaquinta, D. M.; Guan, S.; McFarland, E. W.; Poojary, D. M.; Self, K.; Turner, H. W.; Weinberg, W. H. Angew Chem. Int. Ed. 1999, 38, 484–488 teaches using a probe with concentric tubing for gas delivery/removal and sampling. Only the fixed bed of catalyst being tested is exposed to the reactant stream, with the excess reactants being removed via vacuum. The single fixed bed of catalyst being tested is heated and the gas mixture directly above the catalyst is sampled and sent to a mass spectrometer.

Combinatorial chemistry has been applied to evaluate the activity of catalysts. Some applications have focused on determining the relative activity of catalysts in a library; see Klien, J.; Lehmann, C. W.; Schmidt, H.; Maier, W. F. Angew Chem. Int. Ed. 1998, 37, 3369–3372; Taylor, S. J.; Morken, J. P. Science, April 1998, 280(10), 267–270; and WO 99/34206-A1. Some applications have broadened the information sought to include the selectivity of catalysts. WO 99/19724-A1 discloses screening for activities and selectivities of catalyst libraries having addressable test sites by contacting potential catalysts at the test sites with reactant streams forming product plumes. The product plumes are screened by passing a radiation beam of an energy level to promote photoions and photoelectrons, which are detected by microelectrode collection. WO 98/07026-A1 discloses miniaturized reactors where the effluent is analyzed during the reaction time using spectroscopic analysis.

Some commercial processes have operated using multiple parallel reactors where the products of all of the reactors are combined into a single product stream; see U.S. Pat. No. 5,304,354 and U.S. Pat. No. 5,489,726. Another patent, U.S. Pat. No. 6,149,882 B1 teaches an apparatus having a plurality of vessels and valves and conduits for sequentially sampling the effluent of the vessels or a sample probe positioned next to the effluent to transport sampled fluid to a detector.

Applicants have developed a combinatorial method and apparatus particularly suited for the generation of a plurality of independent effluents. The effluents are generated in parallel, but kept isolated from one another. The effluent may be further processed by, for example, analyzing the composition of the effluent, by further reacting the effluent, by further treating the effluent, and the like. One embodiment of the invention is the evaluation of a plurality of solids where the effluents of all the vessels are simultaneously sampled. Another embodiment of the invention is the evaluation of a plurality of solids where the effluents of all the vessels are sequentially sampled. Multiple solids are contacted with a feed fluid in parallel with the resulting effluents being sampled, simultaneously or sequentially, and then analyzed for changes as compared to the feed fluid. The parallel reactions and the analyses provide a means for the high throughput evaluation of multiple solids or mixtures of solids.

SUMMARY OF THE INVENTION

One purpose of the present invention is to provide an apparatus for generating a plurality of effluents where the apparatus consists of a multiplicity of vessels containing catalysts with each vessel having an inlet and an outlet, each outlet being connected via a conduit to a sampling valve, with the sampling valve also being connected to a set of effluent conduits, a set of bypass conduits, and a set of vent conduits, where each set above has a number at least equal to the number of vessels, at least one selector valve connected to both the set of effluent conduits and the set of bypass conduits, and a processing device is connected to the selector valve. In one specific embodiment of the invention, the vessels are grouped into banks of vessels wherein each bank of vessels is associated with an independent set of: one or more sampling valves, the effluent conduits, the bypass conduits, the vent conduits, the selecting valve and the processing device. The invention is particularly useful to evaluate a plurality of catalysts, and in that embodiment, the processing device is a detector.

Another purpose of the present invention is to provide a method of generating a plurality of effluents where a plurality of catalysts are contained in a set of vessels with each vessel having an inlet and an outlet. The catalysts are contacted, simultaneously, with a feed fluid containing a reactant to generate vessel effluents. The vessel effluents are sequentially sampled and further processed. The further processing may be analyzing the vessel effluents to determine changes in the vessel effluents as compared to the feed fluid or as compared to other vessel effluents. Such analyses may be particularly useful in evaluating a plurality of catalysts.

In a more specific embodiment of the invention, the sampling involves: flowing the vessel effluents simultaneously from the vessels to at least one sampling valve; from the sampling valve(s) through a set of effluent conduits, the number of effluent conduits at least equal to the number of vessels; from the effluent conduits to at least one selector valve; from the selector valve(s) through a set of bypass conduits, the number of bypass conduits at least equal to the number of vessels; from the bypass conduits through the sampling valve(s) for a second time, and from the sampling valve(s) to a set of vent conduits. The selector valve(s) are actuated periodically to sequentially direct selected vessel effluent(s) to one or more processing devices. In another specific embodiment of the invention, the sampling valve(s) are actuated to sequentially trap a portion of the vessel effluents within the effluent conduits. The selector valve(s) are actuated to sequentially direct the trapped vessel effluent(s) to one or more processing devices.

DETAILED DESCRIPTION OF THE INVENTION

An apparatus and a method are provided for combinatorial generation of a plurality of effluents. In general terms, a feed fluid is contacted simultaneously with a plurality of solids where each of the solids is housed in an individual vessel to generate vessel effluents. Each vessel effluent is sampled simultaneously or sequentially with the sampled effluent being retained in a plurality of effluent conduits for analysis. At least a portion of the effluent is further processed. For example, when screening a plurality of solids, a portion of the sampled effluent is introduced into, for example, one or more gas chromatographs for analysis. Changes in the effluents as compared to the feed or to each other are used to determine properties of the plurality of solids being tested. The results of the analysis may also indicate those solids whose performance warrants further investigation.

The plurality of effluents generated by the subject invention are further processed by, for example without limitation, further reacting the effluents, separating the effluents, treating the effluents with an adsorbent, and analyzing the effluent. Any relevant processing device may be used in the processing; reactors, adsorbers, analytical instrumentation, etc. The discussion herein will focus on analyzing the plurality of effluents as is useful in screening a plurality of solids.

The apparatus and method of the present invention may be used to screen the plurality of samples for any property that can be determined through measuring or monitoring the changes between the feed fluid and the effluent. For example, catalytic activity of a solid may be evaluated by analyzing the concentration of the reactants in the feed fluid as compared to the reactants and products of each reactor effluent. With the present invention, those solids showing the greatest conversion to the products or perhaps the greatest selectivity to the desired product could be determined expediently. Similarly, adsorptivity of solids may be evaluated by comparing the concentration of an adsorbate in a feed stream with the concentration of the same adsorbate in each of the reactor effluents. Those solids having the greatest reduction in adsorbate from the feed concentration to the effluent concentration may be quickly identified for further testing and investigation. It is also contemplated that a property of interest may be determined by comparing the effluents to each other as opposed to, or in addition to, the feed fluid. An important benefit of the present invention is that such identifications can be produced rapidly for a large number of samples. In the same amount of time historically required to evaluate a single solid, with the present invention a multiplicity of solids can be evaluated.

Figure 1B:
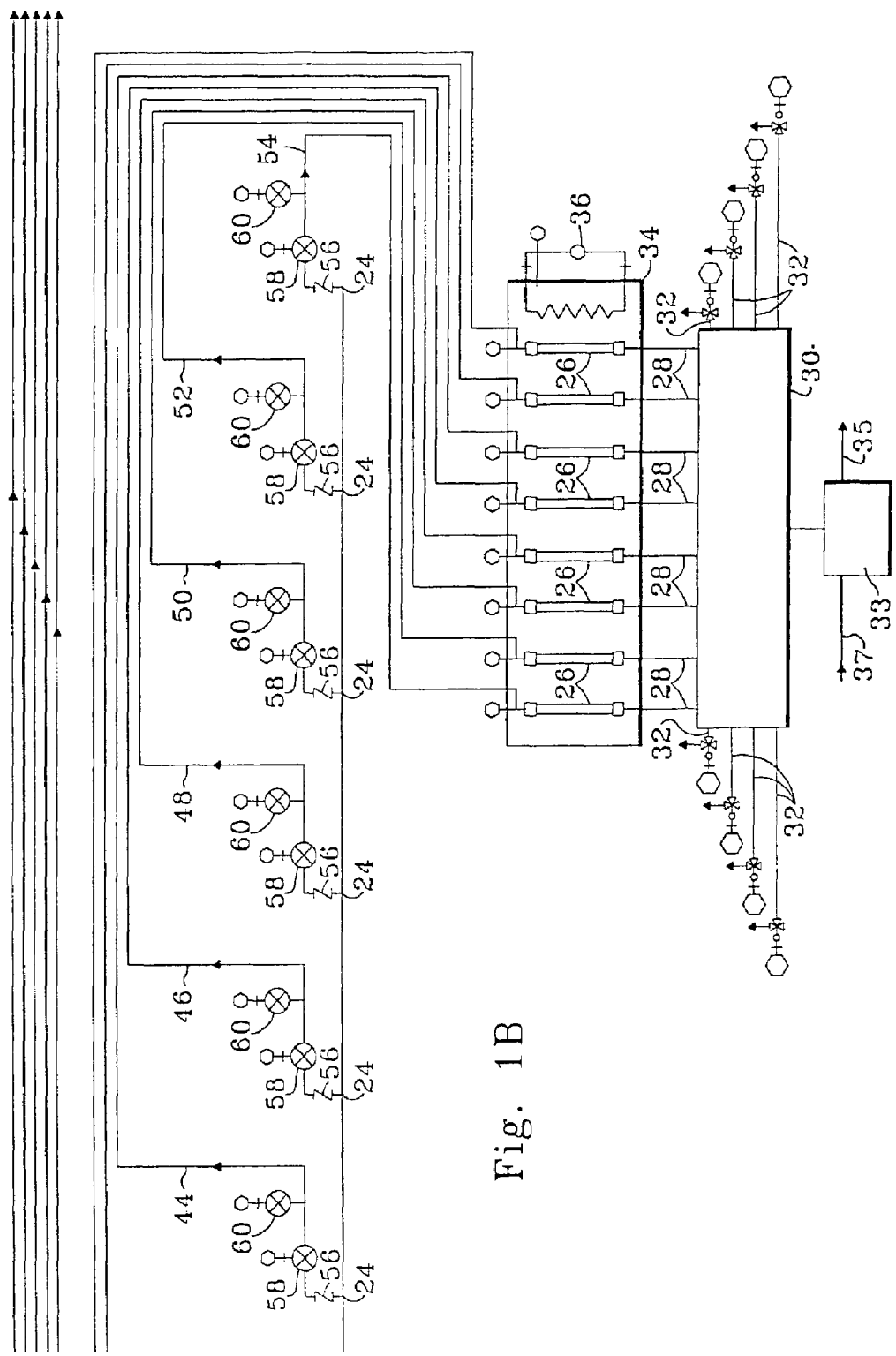
FIG. 1 is an arrangement of views FIG. 1A and FIG. 1B which together comprise a schematic drawing of one embodiment of the invention, an apparatus for rapidly screening solids. The figure shows only the first of multiple banks of reactors.

For ease of explanation, the process and apparatus will be described herein as a 48-reactor system where the reactors are grouped into six banks containing eight reactors in each bank. FIG. 1. shows the source fluids (discussed below) and only the first bank of eight reactors. The other five banks of eight reactors each are not shown. Turning to FIG. 1, the process begins with one or more source fluids 2–8. The source fluids are preferably gaseous, but may be liquid. The gasses may be from cylinders and may be saturated with other components. For purposes of this description, the source fluid is selected to be a gas contained within a cylinder. A set of six selector valves are connected via branch connectors to each of the fluid source lines; i.e., each valve in the set of six is connected via branch connectors to each of the fluid source lines. In the present example, six selector valves are required because there are six banks of reactors. In other applications, the number of selector valves may vary. FIG. 1. shows only the first selector valve 20, corresponding to the first bank of eight reactors. The purpose of the selector valve is to allow for the selection of the source fluid that will be conducted to the reactors. In this example, the selector valves are preferably 10-port valves, although various other devices may be used. The valves are positioned so that the selected source fluids are able to pass rough the valves while the source fluids that are not selected are blocked and unable to pass through the valves. The selector valve and corresponding source fluids allow the solids to be pretreated using a variety of gasses, oxidative, reductive, or neutral, as well as providing the feed containing reactants.

After passing through the selector valve, each of the six source fluid streams is allowed to separate into eight portions through branch connectors. The eight portions of the source fluid stream will be referred to as the reactor feed streams. FIG. 1 shows source fluid stream 22 separating into eight portions by passing through branch connectors 24. The purpose of branch connectors 24 is merely to split the source fluid stream into eight portions. The eight separated portions are not regulated as to mass flow at this point. After separation via branch connectors, the reactor feed streams 40–54 are each separately, yet simultaneously, conducted through a set of associated check valves, 56, a set of associated mass flow controllers, 58, and then a set of associated pressure transducers, 60 i.e., each of the reactor feed streams has an associated dedicated check valve, mass flow controller and pressure transducer. Therefore, a set of eight check valves, 56, a set of eight pressure transducers, 60, and a set of eight mass flow controllers, 58 are used for each of the six banks of reactors. One purpose of the check valves is to aid in preventing backflow. It is contemplated that valves other than check valves may be suitable, and it is preferred that the valve selected be capable of being automated.

The pressure transducers, 60, monitor the pressure of the reactor feed in the eight lines, while the mass flow controllers, 58 are used to individually control the mass flow of each of the reactor feed streams. It is an advantage of the present invention to individually control the mass flow in each of the reactor feed streams. Depending upon the application and the data desired or variables being investigated, the set of feed streams may be controlled to provide the same mass flow to the reactors or they may be controlled at different mass flows. From the mass flow controllers, each reactor feed stream 40–54 is simultaneously introduced to an individual reactor. The reactors, 26, may be of any type used in combinatorial evaluations, with preferred reactors being of the type described in EP 1108467 A2. The number of vessels, i.e., reactors, making up the multiplicity may vary from two vessels to hundreds of vessels. It is preferred to have at least six or twelve vessels in the multiplicity and it is most preferred to have forty-eight vessels in the multiplicity.

The reactors house solids that may interact with the reactor feed stream. For example, the reactors may house catalysts that catalyze a chemical reaction and yield products, or the reactors may house adsorbents that adsorb one or more components from the source fluid. It is within the scope of the invention that the reactor may house a mixture of catalyst and adsorbent. The solids of interest may be present as solid particles or may be supported by solids. Each of the reactors may contain different solids, different mixtures of solids, the same compositional mixture of solids where the components are in different ratios, or the like. Replicates may be included within the array of solids. Typically, the solids will be present in a fixed bed. The reactor feed streams will flow through the interstices of the fixed bed providing contact between the solid and the reactor feed stream. The reactors may be associated with a heater, 34, having a controller, 36, to provide controlled heat to the reactors. Alternatively, individual heaters may be employed.

The effluent from each of the reactors is conducted simultaneously, yet separately, in lines 28 to a sampling system 30 in order to sample the effluents for further processing such as analysis. An advantage of the present invention is that the sampling of the effluent from each reaction may be conducted simultaneously. The benefit of simultaneous sampling is that the results from each reactor are more readily comparable since the solids in each reactor would be exposed to the feed stream for the same period of time. This is perhaps best described using an example. In a 48 reactor array, if the sampling of the 48 effluents were to occur sequentially, and the time needed for each sampling was one minute, there would be a 48 minute time difference between the first reactor being sampled and the last reactor being sampled. Therefore, the overall time the solids in the last reactor would be exposed to the feed stream would be 48 minutes longer than the overall time the solids in the first reactor would be exposed to the feed stream. It is known that the performance of solids may change over the time the solid is in use, or exposed to a feed stream. During the 48 minutes between the sampling of the first and last reactor, performance of the solid in the last reactor may have significantly changed. For example, a catalyst that may have exhibited high initial catalytic activity may show a decline in activity over time, or an adsorbent may have reached its capacity and adsorbate break-through may occur. Therefore, sequential sampling results in data that may not be readily comparable since the time a solid is in use would become a variable as opposed to being virtually identical for all reactors. The same holds true, albeit to a lesser extent, when each bank of reactors has a dedicated detector. The cycle may be reduced from 48 samples taken to 8 samples taken, and perhaps from a 48-minute delay from the first sample to the last sample to only an 8-minute delay. However, the contact time remains a variable unless the sampling is conducted simultaneously for all reactors being compared.

Although simultaneous sampling is usually preferred, specific applications may arise where sequential sampling is the preferred mode for sampling. For example, there may be particular applications where it is not desired to have the effluent remain stagnant in a sample loop until such time as the processing device becomes available. If the effluents contain high molecular weight products, corrosive materials, two immiscible products, or reactive components, the sequential sampling embodiment may be preferred. Sequential sampling may also be preferred when the application calls for a sequential start of the testing of each of the catalysts.

When the effluents are not actively being sampled, each of the effluents is conducted through an independent path, shown as lines 32, to a proper vent system. Depending upon the compounds being employed in the system, waste effluent may be treated to remove, convert, or neutralize specific components before being vented.

Figure 2:
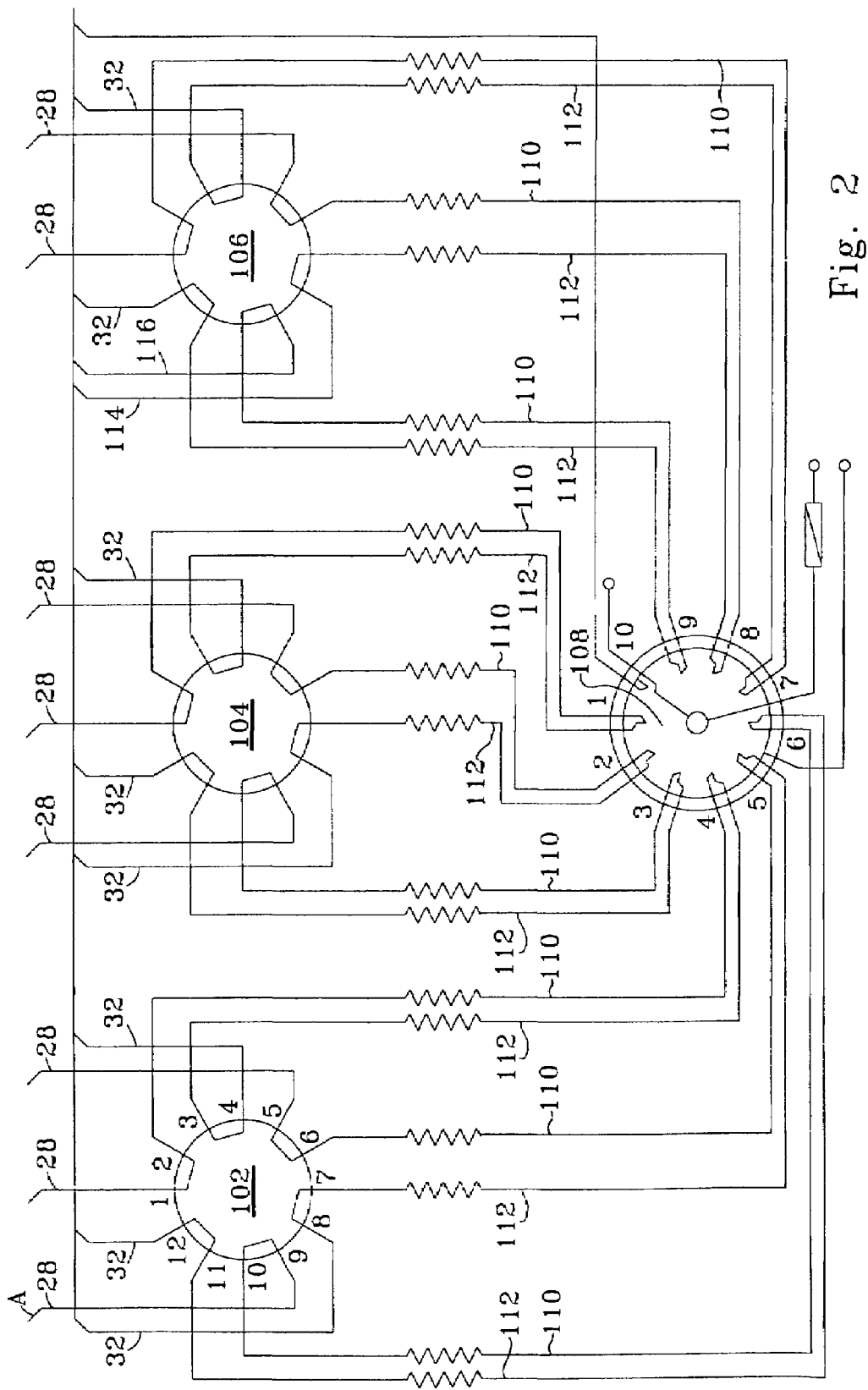
FIG. 2 shows schematically the sampling system as operated in the sampling mode when parallel sampling is employed, and the sampling system when sequential sampling is employed.
Figure 3:
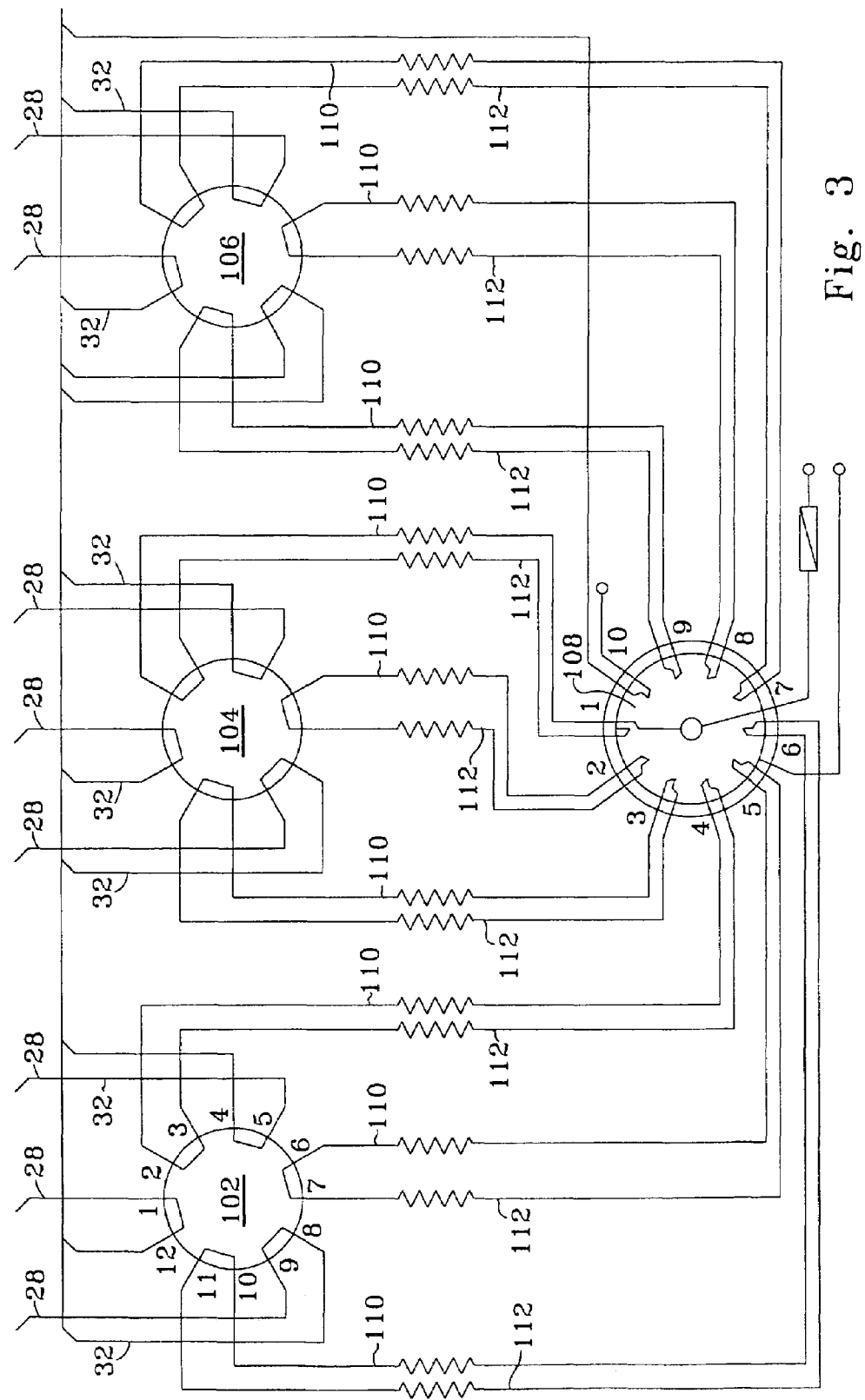
FIG. 3 shows schematically the sampling system as operated in the analysis mode when parallel sampling is employed.

The sampling system is shown in greater detail in FIGS. 2 and 3. When operating with parallel sampling, FIG. 2 shows the valves of the sampling system as positioned in a "sampling mode". In the sampling mode, the reactor effluents are simultaneously directed to flow through the plurality of effluent conduits. One suitable type of effluent conduit is a sample loop. The flow through the effluent conduits remains dynamic and after passing through the effluent conduits, the effluents are conducted to vent. The series valves controlling the path of the fluid flows are actuated at the same time to simultaneously allow effluent to flow through the effluent conduits, and then to simultaneously trap a portion of each effluent within an effluent conduit. FIG. 3 shows the valves of the sampling system as positioned in an "analysis mode". In the analysis mode, the flows through the effluent conduits are blocked, thereby trapping a portion of each of the effluents previously flowing through the effluent conduits. The portions of the effluents trapped within the effluent conduits may then be conducted, sequentially or in parallel to one or more processing devices such as analytic systems or detectors. For ease of explanation, a gas chromatograph will be the analytical detection device described herein. However, other analytical techniques such as liquid chromatography including high pressure liquid chromatography, infrared spectroscopy, uv-vis spectroscopy, ultraviolet spectroscopy, visible spectroscopy, fluorescence spectroscopy, infrared thermography, nuclear magnetic resonance, paramagnetic resonance, X-ray adsorption, X-ray photoelectron spectroscopy, Raman spectroscopy, mass spectroscopy, and combinations thereof may be similarly employed.

Turning now to FIG. 2, which depicts the sampling mode of the parallel sampling embodiment, effluent lines 28 conduct reactor effluent from the first bank of eight reactors to a series of three 12-port valves, 102, 104, and 106, termed "sampling valves" herein. Each bank of eight reactors has a corresponding series of three 12-port valves for a total of 18 12-port sampling valves, however, FIGS. 2 and 3 depict the equipment used for only the first bank of eight reactors. Depending on the application, as few as one sampling valve is required. Simultaneously, each reactor effluent enters a first port of a valve and exits a second port of that valve conducting the effluents into effluent conduits 110. All effluent conduits 110 conduct the effluents to valve 108. Each effluent, after having passed through a dedicated effluent conduit, enters valve 108. Valve 108 may be a Valco 10-port STF-configuration valve which allows the non-selected streams to return to their own vents or sources rather than being dead-ended or trapped. A more detailed discussion of valve 108 is found with reference to FIG. 3 below. In the sampling mode, the internals of valve 108 conduct the reactor effluents to bypass conduits 112. The bypass conduits 112 independently conduct the reactor effluents back to valve 102, 104, or 106 where, again, the effluent enters the valve through a first port and exits through a second port which is connected to lines 32. Lines 32 independently conduct the effluent to vent. Thus, in the sampling mode, each of the reactor effluents is simultaneously, yet independently, flowed through effluent conduits and then conducted to vent.

A trace of the path of a single reactor effluent through the valves is as follows. Reactor effluent "A" is conducted through line 28 to port 102-9 of valve 102. The internals of valve 102 route reactor effluent A to port 102-10 of valve 102, which is connected to effluent conduit 110. Effluent conduit 110 conducts reactor effluent A to port 108-6 of valve 108. Port 108-6 is internally configured to route reactor effluent A directly to bypass conduit 112. Bypass conduit 112 is connected to port 102-11 of valve 102. The internals of valve 102 route reactor effluent A to port 102-12 of valve 102 which is connected to line 32 and conducts effluent A to vent.

In the preferred sampling mode above, each reactor effluent utilizes four ports of one of the 12-port valves. Of the total of 36 ports available on the three 12-port valves, the eight effluent streams utilize 32 ports thereby leaving four ports available for another fluid stream. This additional stream may be a calibration stream for the detector or perhaps a reference standard. In FIG. 2 the additional stream is conducted through line 114 to valve 106. The stream then follows an identical path to that of the reactor effluent streams, with stream 116 ultimately conducting the additional stream to vent. While preferred, provisions for such an additional stream are not a requirement. Therefore, the exact type of valves used for valves 102, 104, and 106 will vary with the application. It is not necessary that valves 102, 104, and 106 be 12-port valves. The valves may be any type of device or valve that allows for the simultaneous direction of fluid flow to a set of independent effluent conduits. Although not necessary, it is also preferred that the same valves allow for the simultaneous direction of fluid flow from a set of independent bypass conduits to vent lines. A second set of valves may be employed for the latter function if advantageous in a specific application.

FIG. 2 also depicts the sequential sampling embodiments. As described above, effluent is flowing through effluent conduits 110, through selection valve 108, and through bypass conduits 112. In the sequential sampling embodiment, selection valve 108 is actuated to direct the effluent flowing through a first port to the processing device. The rest of the effluents remain flowing through sampling valves 102, 104, and 106, effluent conduits 110, selection valve 108, bypass conduits 112, again through sampling valves 102, 104 and 106, and through lines 32. After a period of time, selection valve 108 is actuated to direct the effluent flowing through a second port to the processing device. Again, the rest of the effluents remain flowing through sampling valves 102, 104, and 106, effluent conduits 110, selection valve 108, bypass conduits 112, again through sampling valves 102, 104 and 106, and through lines 32. The process continues at least until all the effluents of interest have been processed. The cycling of the selection valve 108 may continue in order to process the effluents over time. It is within the scope of the invention to have the processing device located in a remote location such as an analytical laboratory. The isolated effluents, after passing through the selector valve, may be condensed into containers and processed at a remote location such as an analytical laboratory.

In another sequential sampling embodiment, sampling valves are used to sequentially trap a portion of each effluent in the effluent conduits. FIG. 2, which can also be used to generally depict this sequential sampling embodiment, effluent lines 28 conduct reactor effluent from the first bank of eight reactors to the series of sampling valves, 102, 104, and 106. However, in this embodiment, a sampling valve with additional ports or internal workings may be employed instead of those shown in FIG. 2. One of ordinary skill in the art would understand the appropriate valve to employ in this embodiment. Simultaneously, each reactor effluent enters a first port of a valve and exits a second port of that valve conducting the effluents into effluent conduits 110. All effluent conduits 110 conduct the effluents to selection valve 108. The internals of selection valve 108 conduct the reactor effluents to bypass conduits 112. The bypass conduits 112 independently conduct the reactor effluents back to valve 102, 104, or 106 where, again, the effluent enters the valve through a first port and exits through a second port which is connected to lines 32. Lines 32 independently conduct the effluent to vent. The sampling valves are actuated so that a first effluent is trapped within the first effluent conduit and the first bypass conduit, then the sampling valves are actuated so that a second effluent is trapped within the second effluent conduit and the second bypass conduit, and so on. The selection valve 108 is used to sequentially direct the effluents trapped within the effluent conduits to a processing device where the effluents are sequentially processed. The selection valve may be directing selected effluents to a processing device before all the portions of effluents have been trapped. This embodiment allows for great flexibility by allowing for specific individual effluents to be trapped at specific intervals or points in time and then storing the portion of effluent until further processing is available.

Returning now to the simultaneous sampling embodiment of the invention, FIG. 3 depicts the analysis mode of the parallel sampling embodiment. Valves 102, 104, and 106 are positioned so that a portion of each of the reactor effluent that was previously flowing through the effluent conduits 110 is retained within the effluent conduits 110. Since the valves may be actuated at the same time, the capture of fluid within the effluent conduits occurs simultaneously thereby effecting a simultaneous sampling of all the reactor effluents. The reactor effluents are retained within the effluent conduits until sequentially analyzed as discussed below, or analyzed in parallel. FIG. 3 shows lines 28, which conduct the reactor effluent from the reactors to valves 102, 104, and 106. In the analysis mode of FIG. 3 however, the ports connected to lines 28 are internally routed to the ports connected to vent lines 32, and not to effluent conduits 110 as shown in FIG. 2 for the sampling mode. Therefore, the reactor effluent flows through lines 28, through samples valve 102, 104, or 106, and then through lines 32 to vent. In the analysis mode, the reactor effluents are not all simultaneously flowing through effluent conduits 110. The ports that are connected to effluent conduits 110 are internally routed to the ports that are connected to the corresponding bypass conduits.

Valve 108, in addition to being connected to each of the sets of effluent conduits 110 and bypass conduits 112, is connected to an analytical instrument and to a vent line. For purposes of discussion here, the analytical instrument is a gas chromatograph (GC). Valve 108 may be positioned to interrupt the connection of one specific effluent conduit to the corresponding bypass conduit for a selected reactor effluent. The effluent conduit would become instead, connected to the GC and the bypass conduit would become connected to the vent line. A pump of the GC could draw a portion of the selected reactor effluent from the effluent conduit through valve 108 and into the GC for analysis. Each reactor effluent could be selected sequentially for GC analysis. Similarly, any additional stream such as a calibration fluid or a reference standard, as discussed above, that is retained within an effluent conduit 110 may be analyzed using the GC.

In the analysis mode, the portion of reactor effluent "A" retained in effluent conduit 110 is first held as a static fluid in a closed path that is made up of effluent conduit 110, valve 102 including ports 102-10 and 102-11, bypass conduit 112, and valve 108 including port 108-6. When port 108-6 is selected using valve 108, effluent conduit 110 becomes connected to the GC and bypass conduit 112 becomes connected to a vent. A pump draws a portion of reactor effluent A from effluent conduit 110 through port 108-6 and into the GC. It is also contemplated that a flush fluid may be introduced through the vent line to displace the effluent and cause effluent to be conducted to the GC. Because bypass conduit 112 is now connected to a vent line, a portion of reactor effluent A may be withdrawn from effluent conduit 110 without significant force. After a portion of reactor effluent A has been conducted to the GC, valve 108 may be returned to a null position. When the GC is ready to analyze another sample, valve 108 is positioned to select another reactor effluent. Each reactor effluent from the bank of eight reactors is analyzed sequentially. In the preferred embodiment, each bank of reactors would have a dedicated GC, so for the example of the array having six banks of eight reactors each, six GCs overall would be utilized. Within a bank of reactors, the effluents would be analyzed sequentially, but each of six GCs would operate simultaneously so that the overall elapsed time to analyze all 48 reactor effluents over the six GCs would be equal to the time needed for only eight analyses.

It is contemplated that the feed fluid may be comprised of a gas stream that has been passed through a component most conveniently available in a liquid form in order for the gas stream to carry a portion of the component to the solids contained in the vessels. This embodiment is shown in FIG. 1 as optional system 66. Within system 66, a gaseous source fluid is conducted through line 10 into vessel 68. Vessel 68 contains a liquid component, or mixture of components, which is fed to vessel 68 through line 78. The source fluid is allowed to bubble through the liquid, absorbing a portion of the component. The vessels may be considered to be saturators. Additional vessels may be employed, 70 and 72, allowing the source fluid to bubble through additional quantities of the liquid component(s) via lines 80 and 82. A heater or cooler, 76, may be employed with a control device 74 to maintain the vessels at a desired temperature. A liquid bath may be employed to control the temperature of the vessels. Lines 10, 80 and 82 may be equipped with a check valve and a pressure sensor. The feed fluid containing both the gaseous source fluid and a portion of the components contained in the vessels is conducted via line 88 to the source fluid selector valve(s) 20. Line 88 may be equipped with apparatus to analyze the composition of the feed fluid for comparison to the composition of the vessel effluents.

The above description is focused on a preferred embodiment of the invention. One of ordinary skill in the art would readily understand how to extrapolate the above description to various embodiments of the invention. For example, various other different types of detectors may be employed instead of or in combination with the gas chromatograph. Suitable detectors include a gas chromatograph, an infrared detector, a uv-vis detector, an ultraviolet detector, a visible detector, fluorescence detector, an infrared thermography detector, a nuclear magnetic resonance detector, a paramagnetic resonance detector, a X-ray adsorption detector, a X-ray photoelectron detector, a Raman detector and combinations thereof. Similarly, other processing devices besides a detector may be used to process the isolated effluents. A reactor may be used to further react the effluents, a separator may be used to separate the effluents, or a treatment vessel containing, for example, an adsorbent may be used to treat the effluents.

What is claimed is:

1. A method for generating and processing a plurality of effluents comprising:

a) contacting, simultaneously, at least one fluid containing a reactant with a multiplicity of catalysts, each catalyst contained in one of a multiplicity of vessels to generate a plurality of effluents wherein the plurality of generated effluents corresponds to the multiplicity of the catalysts in the multiplicity of vessels;

b) flowing, simultaneously, the plurality of effluents from the multiplicity of vessels through at least one sampling valve, said sampling valve having X inlets and Y outlets, where X is not less than the number of effluents;

c) collecting a portion of at least a first effluent at a time T1 by actuating the sampling valve to close a first loop comprising the sampling valve, a first effluent conduit, the selection valve, and corresponding first bypass conduit; and collecting a portion of at least a second effluent at a time T2 by actuating the sampling valve to close a second loop comprising the sampling valve, a second effluent conduit, the selection valve, and a corresponding second bypass conduit;

d) directing, sequentially, at least a portion of the collected effluents to a processing device by activating the selection valve; and e) sequentially processing the effluents using the processing device.

2. The method of claim 1 wherein the processing is selected from the group consisting of analyzing the effluents, reacting the effluents and treating the effluents.

3. The method of claim 1 where the effluents flowing through the selection valve are directed to the processing device by collecting the effluents into containers and transporting the containers to the processing device.

4. The method of claim 1 wherein said vessels are grouped into banks of vessels thereby generating multiple pluralities of effluents, each plurality of effluents undergoing method steps (b) through (e) of claim 1.

5. The method of claim 1 wherein the multiplicity of vessels is comprised of at least six vessels.

6. The method of claim 1 wherein the multiplicity of vessels is comprised of at least twelve vessels.

7. The method of claim 1 further comprising conducting the remainder of the collected portions of effluents from the first or second loop though a venting conduit which is in fluid communication with the selection valve in order to clear the loop.

8. The method of claim 2 wherein the step of analyzing the effluents is performed using a technique selected from the group consisting of gas chromatography, liquid chromatography including high pressure liquid chromatography, mass spectroscopy, infrared spectroscopy, uv-vis spectroscopy, ultraviolet spectroscopy, visible spectroscopy, fluorescence spectroscopy, infrared thermography, nuclear magnetic resonance, paramagnetic resonance, X-ray adsorption spectroscopy, X-ray photoelectron spectroscopy, Raman spectroscopy and combinations thereof.

9. The method of claim 1 further comprising saturating the fluid containing a reactant with another fluid prior to the contacting.

10. The method of claim 1 further comprising heating the vessels.

11. The method of claim 10 further comprising controlling the heating of the vessels.

12. The method of claim 1 wherein the processing comprises analyzing the effluents and further comprising determining changes in the effluents as compared to the fluid containing a reactant.

13. The method of claim 12 wherein the changes determined include changes in composition of the effluents as compared to the fluid containing a reactant.

14. The method of claim 1 further comprising weighing each of the catalysts prior to contacting with the fluid containing a reactant.

15. The method of claim 1 further comprising passing a gaseous stream through a body of liquid to form the fluid containing a reactant prior to contacting with the catalysts.

16. The method of claim 15 further comprising analyzing the fluid formed by passing a gas stream through a body of liquid to determine the composition of the fluid prior to contacting with the catalysts.

17. The method of claim 1 further comprising repeating method steps (b) through (e).

18. A method for generating and processing a plurality of effluents comprising:

a) contacting, simultaneously, at least one fluid containing a reactant with a multiplicity of catalysts, each catalyst contained in one of a multiplicity of vessels to generate a plurality of effluents wherein the plurality of generated effluents corresponds to the multiplicity of the catalysts in the multiplicity of vessels;

b) flowing, simultaneously, the plurality of effluents from the multiplicity of vessels through at least one sampling valve said sampling valve having X inlets and Y outlets, where X is not less than the number of effluents;

c) adjusting the sampling valve to direct:
   i. a first effluent into a first of a set of effluent conduits, through a selection valve wherein the selection valve is in fluid communication with the set of effluent conduits and a set of bypass conduits, through a first of the set of bypass conduits, through the sampling valve again and through a first of a set of vent conduits;
   ii. the remainder of the effluents through the sampling valve and into a set of vent conduits in fluid communication with the sampling valve;

d) adjusting, at a time T1, the sampling valve to trap a portion of the first effluent within a first closed loop comprising the sampling valve, the first effluent conduit, the selection valve, and the corresponding first bypass conduit;

e) adjusting the sampling valve to direct:
   ii. a second effluent into a second of a set of effluent conduits, through the selection valve in fluid communication with the set of effluent conduits and the set of bypass conduits, through a second of the set of bypass conduits, through the sampling valve, and through the second of a set of vent conduits;
   iv. the first effluent and the remainder of the effluents through the sampling valve and into a set of vent conduits in fluid communication with the sampling valve;

f) adjusting, at a time T2, the sampling valve to trap a portion of the second effluent within a second closed loop comprising the sampling valve, the second effluent conduit, the selection valve, and the corresponding second bypass conduit, where T1 is not equal to T2;

g) continuing to sequentially trap a portion of each of the effluents within closed loops comprising the sampling valve, the corresponding effluent conduit and bypass conduit, and the selection valve by adjusting the sampling valve;

h) directing, sequentially, the effluents trapped within the closed loops to a processing device using the selection valve; and i) sequentially processing the effluents using the processing device.

19. The method of claim 18 wherein the processing is selected from the group consisting of analyzing the effluents, reacting the effluents and treating the effluents.

20. The method of claim 18 wherein said vessels are grouped into banks of vessels thereby generating multiple pluralities of effluents, each plurality of effluents undergoing method steps (b) through (i) of claim 1.

21. The method of claim 19 wherein the step of analyzing the effluents is performed using a technique selected from the group consisting of gas chromatography, liquid chromatography including high pressure liquid chromatography, mass spectroscopy, infrared spectroscopy, uv-vis spectroscopy, ultraviolet spectroscopy, visible spectroscopy, fluorescence spectroscopy, infrared thermography, nuclear magnetic resonance, paramagnetic resonance, X-ray adsorption spectroscopy, X-ray photoelectron spectroscopy, Raman spectroscopy and combinations thereof.

* * * * *